(12) United States Patent
Weitzner et al.

(10) Patent No.: US 9,265,525 B2
(45) Date of Patent: Feb. 23, 2016

(54) METHODS AND DEVICES FOR TRAVERSING AN ANATOMIC WALL

(75) Inventors: Barry Weitzner, Acton, MA (US); Paul J. Smith, Smithfield, RI (US); John B. Golden, Norton, MA (US); Michal Weisman, Allston, MA (US); Stephen J. Perry, Shirley, MA (US); Katie Krueger, Merrimack, NH (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1462 days.

(21) Appl. No.: 12/122,801

(22) Filed: May 19, 2008

(65) Prior Publication Data

US 2008/0287740 A1 Nov. 20, 2008

Related U.S. Application Data

(60) Provisional application No. 60/938,928, filed on May 18, 2007.

(51) Int. Cl.
| | |
|---|---|
| *A61B 17/00* | (2006.01) |
| *A61B 1/06* | (2006.01) |
| *A61B 17/34* | (2006.01) |
| *A61B 19/00* | (2006.01) |

(52) U.S. Cl.
CPC ......... *A61B 17/3423* (2013.01); *A61B 17/3417* (2013.01); *A61B 2017/00278* (2013.01); *A61B 2017/00876* (2013.01); *A61B 2017/3425* (2013.01); *A61B 2017/3486* (2013.01); *A61B 2017/3488* (2013.01); *A61B 2019/307* (2013.01)

(58) Field of Classification Search
CPC .......... A61B 17/3415; A61B 17/3417; A61B 17/3421; A61B 17/3423; A61B 2017/3419; A61B 1/00154; A61B 17/0057; A61B 2017/00606
USPC ................. 606/192, 213; 623/23.65; 600/170
See application file for complete search history.

(56) References Cited

U.S. PATENT DOCUMENTS

| | | | |
|---|---|---|---|
| 5,297,536 A | 3/1994 | Wilk | |
| 6,572,629 B2 | 6/2003 | Kalloo et al. | |
| 6,620,181 B1 * | 9/2003 | Bonutti .................. | 606/190 |
| 2001/0049497 A1 | 12/2001 | Kalloo et al. | |
| 2003/0229296 A1 | 12/2003 | Ishikawa et al. | |
| 2004/0082850 A1 | 4/2004 | Bonner et al. | |
| 2005/0107664 A1 | 5/2005 | Kalloo et al. | |
| 2005/0277945 A1 | 12/2005 | Saadat et al. | |

(Continued)

FOREIGN PATENT DOCUMENTS

| | | |
|---|---|---|
| WO | WO 02/085225 A1 | 10/2002 |
| WO | WO 03/097124 A2 | 11/2003 |
| WO | WO 2007/038715 A1 | 4/2007 |

OTHER PUBLICATIONS

International Search Report and Written Opinion for PCT/US2008/063975 dated Feb. 9, 2009.

*Primary Examiner* — Katherine Rodjom
(74) *Attorney, Agent, or Firm* — Bookoff McAndrews, PLLC

(57) ABSTRACT

Disclosed herein are various systems and methods for traversing an anatomic wall. A system can include a port that mates with an anatomic wall and provides a lumen for the passage of a guide tube of a transluminal device. The port can inhibit the passage of biological materials through the anatomic wall. Further described herein are methods for implanting the port and/or for inserting the transluminal device into a body cavity.

38 Claims, 11 Drawing Sheets

(56) References Cited

U.S. PATENT DOCUMENTS

| | | |
|---|---|---|
| 2006/0258909 A1 | 11/2006 | Saadat et al. |
| 2007/0203396 A1* | 8/2007 | McCutcheon et al. ........ 600/173 |
| 2008/0086080 A1* | 4/2008 | Mastri et al. ............... 604/95.03 |

* cited by examiner

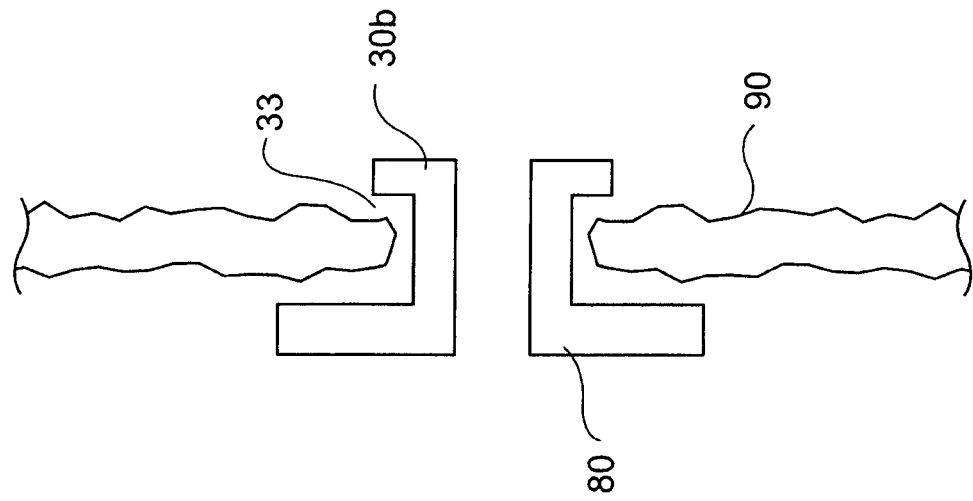
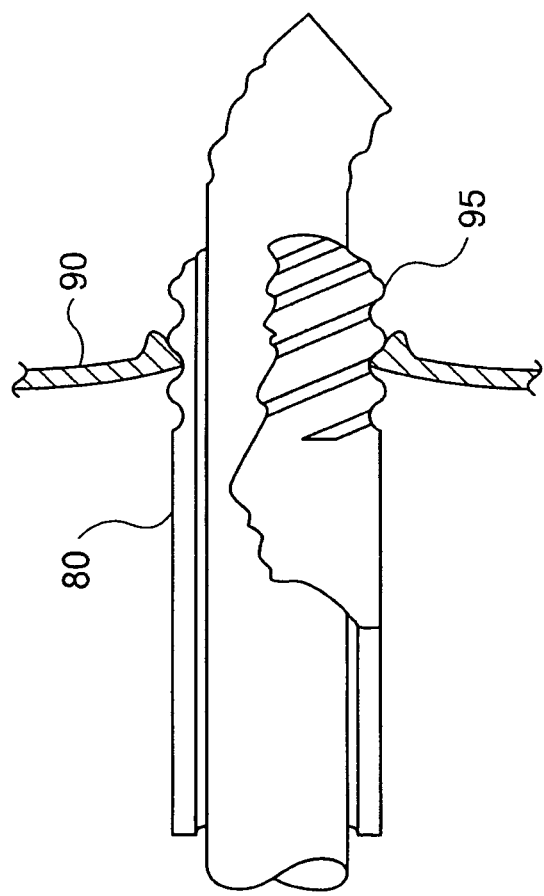
FIG. 8B
FIG. 8A

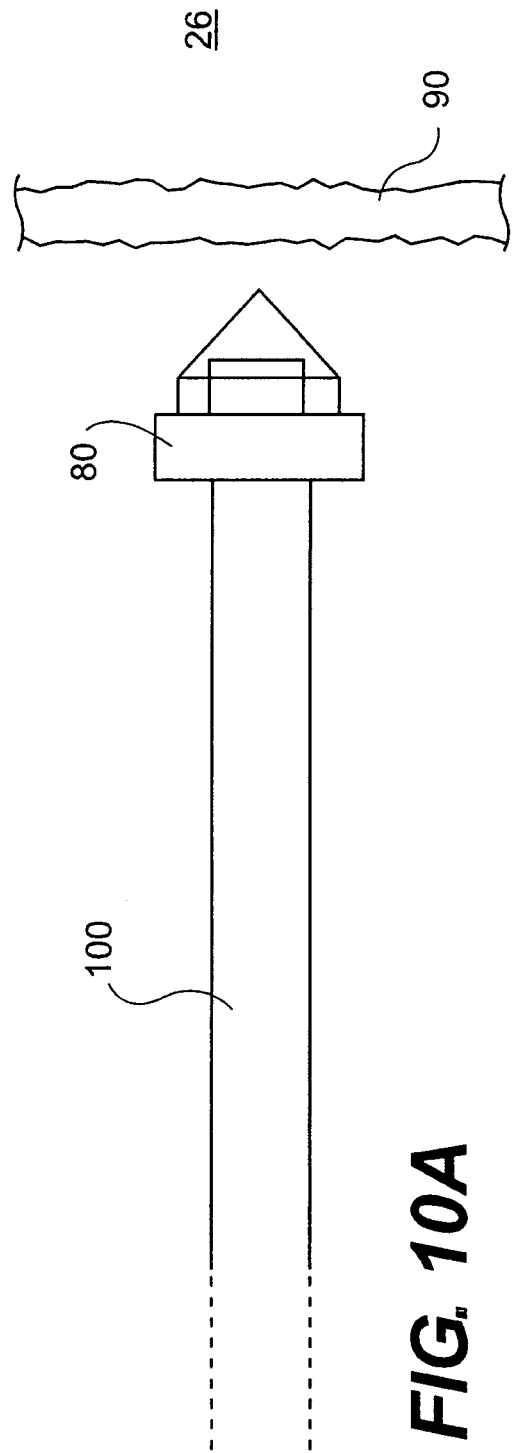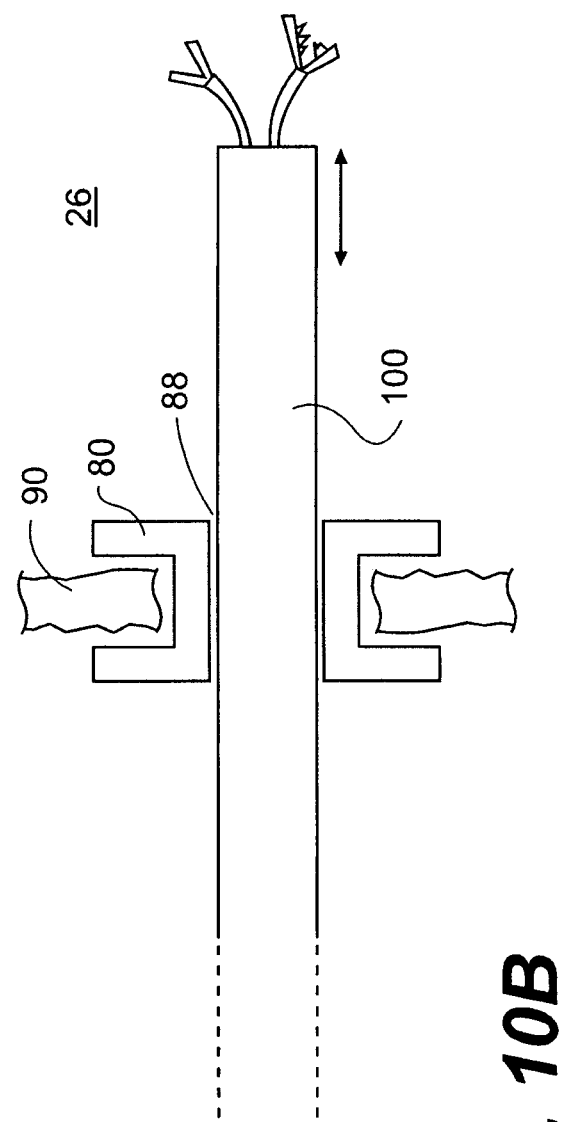

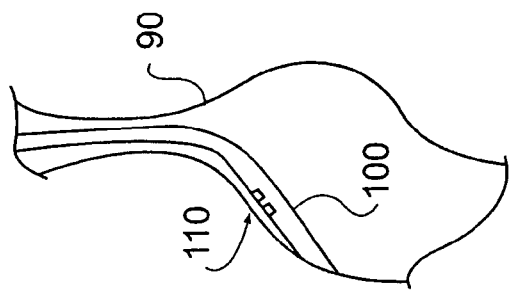
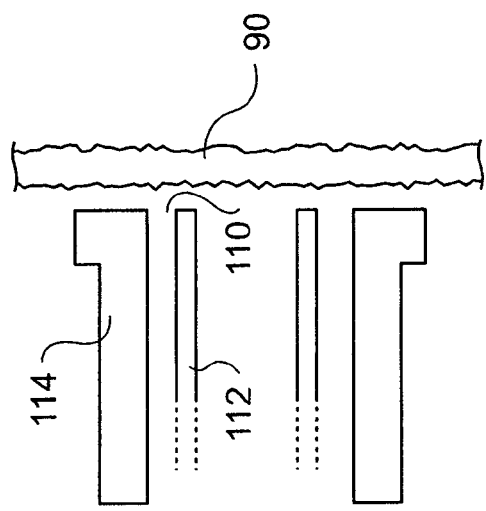
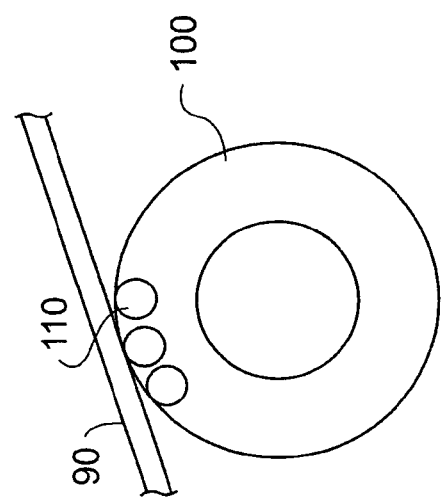
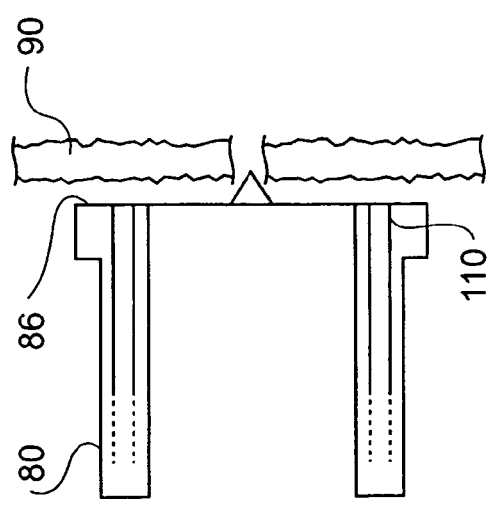

METHODS AND DEVICES FOR TRAVERSING AN ANATOMIC WALL

This application claims priority to U.S. Provisional Application Ser. No. 60/938,928 entitled "METHODS AND DEVICES FOR TRAVERSING AN ANATOMIC WALL" filed May 18, 2007.

BACKGROUND OF THE INVENTION

Traditionally, open surgical techniques or laparoscopic procedures have been used to access the abdominal cavity. Such procedures require incision through the skin and underlying muscle and peritoneal tissue and can result in significant patient recover periods and post-surgical scarring.

Other approaches have been considered, including access through a natural body orifice. For example, an endoscope can be directed through a patient's mouth to gain access to a body cavity. Although the growing capabilities of such therapeutic devices allow physicians to perform an increasing variety of surgeries through minimally invasive routes, further refinements may allow even less traumatic surgical access and/or performance of traditional open surgical or laparoscopic procedures through a natural orifice. Accordingly, methods and devices that enhance access, particularly improvements that facilitate access through anatomic structures, would be beneficial.

SUMMARY OF THE INVENTION

Disclosed herein are methods and devices for traversing an anatomic wall. In one aspect, a system includes a transluminal device configured for insertion through a natural orifice and a port for permitting access through an anatomic wall. The port can mate with an anatomic wall and can permit passage of the transluminal device through the anatomic wall, while inhibiting the passage of biomaterials, thereby reducing possible contamination and infection.

In one embodiment, the port is integrated with a transluminal device. The transluminal device can include an elongate guide tube extending between a proximal portion and a distal portion and at least one channel for the passage of a tool. The distal portion of the guide tube can include at least one mating element for mating the guide tube with an anatomic wall. In another aspect, the guide tube includes a proximal and a distal tissue mating element. In use, the guide tube can be inserted through an opening in an anatomic wall until the wall is positioned between the proximal and distal tissue mating elements. Once the anatomic wall is so positioned, the tissue mating elements can inhibit further insertion or withdrawal of the guide tube.

In one aspect, at least one of the tissue mating elements can be increased in cross-sectional width to mate the guide tube with the anatomic wall. In another aspect, the distal mating element can move between an insertion configuration and a mating configuration. In the insertion configuration, the distal mating element at least partially blocks the at least one channel in the guide tube. In the mating configuration the distal mating element can increase in cross-sectional width and open the at least one channel.

In addition to mating with the anatomic wall, the mating elements and/or the outer surface of the guide tube can create a seal between the guide tube and the anatomic wall. For example, the mating elements can inhibit the passage of biological materials between the outer surface of the guide tube and the anatomic wall.

Further described herein are transluminal systems including a guide tube and a stand alone port. The port can include a tissue contact surface and at least one mating element for mating with an anatomic wall. In addition, the port can including a lumen for receiving at least a portion of the elongate guide tube. In one aspect, the guide tube and port are not mated, or are moveably mated to allow movement of the guide tube through the lumen.

The port can include a distal surface. In one aspect, an obturator defines the distal surface and can inhibit passage of biological material into the lumen. After implanting the port, the obturator can be opened. For example, the obturator can be broken, pierced, dissolved, degraded, detached, and/or moved away from the lumen of the port. In addition to providing an obturator, the distal surface can facilitate insertion of the port at least partially through an anatomic wall. In one such aspect, the distal surface is tapered. In yet another aspect, the distal surface can additionally, or alternatively, define a tissue mating element.

The lumen within the port and/or the outer surface of the guide tube can, in one aspect, include a seal. For example, the size (e.g., diameter) and or shape of the lumen can be varied to match the size and/or shape of the guide tube. In one aspect, the seal is a check valve, wiper seal, and/or membrane.

In another embodiment, the transluminal system can include a body that extends from an opening in a patient to the port and defines a passageway for insertion of the guide tube. In one aspect, the passageway can provide a barrier to inhibit the ingress of biological materials.

In yet another embodiment, a transluminal system comprises an outer guide tube and an inner elongate body. The outer guide tube can include an outer surface and an inner lumen defining an inner surface. The inner body can be positioned within the outer body and can include at least one channel for the passage of a surgical tool. The inner body can be configured to move relative to the outer body. The system can further include a pump and a passageway between the inner body and outer guide tube where the pump can create a vacuum.

In one aspect, the passageway between the inner body and the outer guide tube extends to a distal opening. Establishing a vacuum between the inner body and the outer guide tube can create suction at the distal opening for mating the transluminal system with tissue. In another aspect, the suction can create a seal between tissue and the transluminal system.

BRIEF DESCRIPTION OF THE DRAWINGS

The accompanying drawings, which are incorporated in and constitute a part of this specification, illustrate exemplary embodiments of the invention and, together with the description, serve to explain the principles of the invention.

FIG. 8A is a side view of another embodiment of a port described herein;

FIG. 8B is a side view of yet another embodiment of a port described herein;

FIG. 10A is a side view of another embodiment of a port described herein;

FIG. 10B is a cross-sectional view of the port of FIG. 10A mated with an anatomic wall;

FIG. 13 is a cross-sectional view of one exemplary embodiment of a device described herein;

FIG. 14 is a cross-sectional view of another embodiment of the device of FIG. 13;

FIG. 15A is a partially transparent view of one exemplary embodiment of a transluminal device described herein; and FIG. 15B is a cross-sectional view of the device of FIG. 15A.

DETAILED DESCRIPTION

Described herein are surgical systems, methods, and devices for traversing an anatomic wall, such as, for example, the gastrointestinal wall. In one aspect, a system includes a transluminal device configured for insertion through a natural orifice and a port for permitting access through an anatomic wall. The port can mate with an anatomic wall and can permit passage of the transluminal device through the anatomic wall, while inhibiting the passage of biomaterials, thereby reducing possible contamination and infection.

In one aspect, the port is mated with or defined by a portion of the transluminal device. The transluminal device can include a guide tube having at least one mating element for mating with an anatomic wall. For example, the guide tube can include a proximal and a distal mating element, which are configured to increase in cross-sectional width when placed on opposite sides of an anatomic wall. The distal end of the guide tube can include a obturator having a tapered configuration. In use, the obturator can expand an opening created in an anatomic wall. Once the obturator is moved through the anatomic wall, the obturator can be detached, broken, pierced, degraded, dissolved, and/or opened to open the distal end of the transluminal tool and allow the passage of a surgical instrument.

Further described herein are stand-alone or detachable ports through which a transluminal device can be passed. The port body can include at least one mating element for mating with an anatomic wall and a lumen for the passage of a guide tube. The port lumen can be configured to allow the guide tube to rotate and/or move longitudinally therethrough. In one aspect, the port includes a seal to inhibit the passage of biological materials as the guide tube passes through the lumen. In another aspect, the port can include a sheath that extends between an opening in a patient and the lumen.

The transluminal devices can include the variety of devices that can be introduced into the body, for example, through a body orifice (e.g., the rectum, mouth, vagina) and maneuvered to target location within a patient. In one aspect, a transluminal device can include a flexible guide tube having at least one inner lumen for the delivery of a tool(s), such as, for example, an endoscope and surgical instruments. Alternatively, such tools can be defined by or integrated with a portion of the guide tube. Exemplary guide tubes and tools are described, for example, in U.S. application Ser. Nos. 11/946,779; 11/946,790; 11/946,799; 11/946,807; 11/946,812; and 11/946,818, which are incorporated herein by reference. While transluminal access is discussed herein, the various described devices may also or alternatively rely on percutaneous or surgical access.

Figure 1:
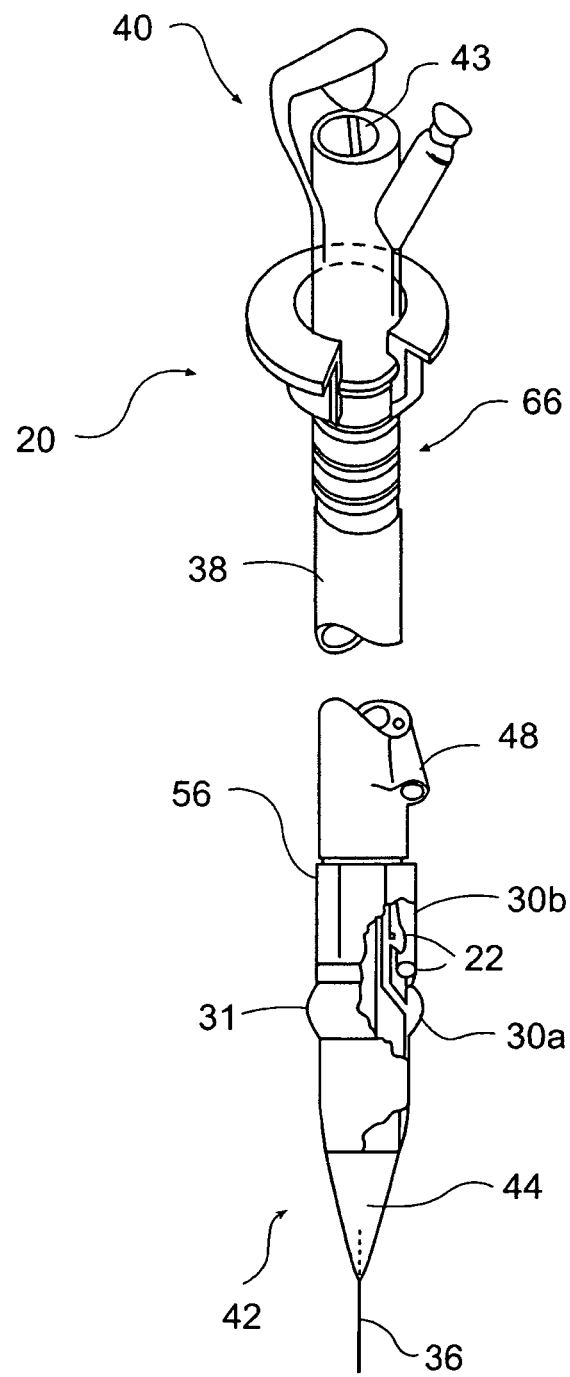
FIG. 1 is a partial side view of one exemplary embodiment of a transluminal device described herein.
Figure 2A:
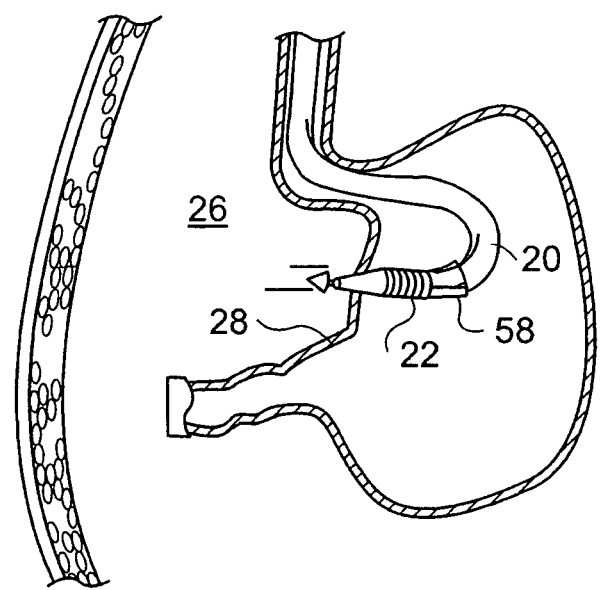
FIG. 2A is a partially transparent view of a transluminal through a gastric wall.
Figure 2B:
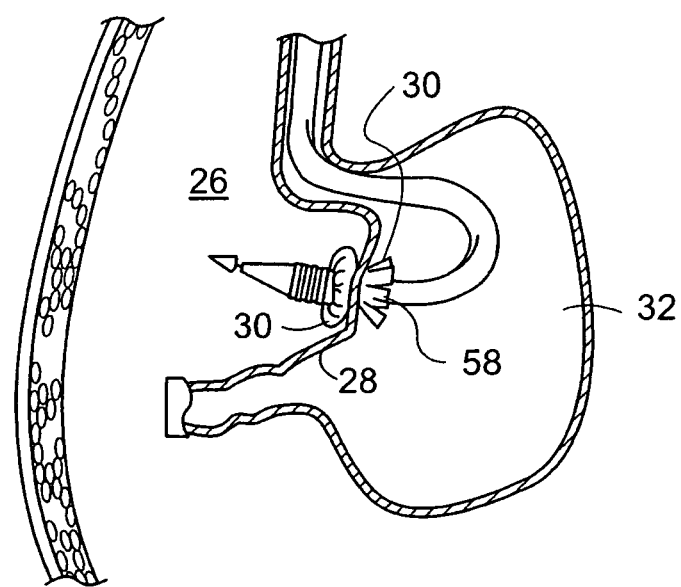
FIG. 2B is a partially transparent view of the transluminal device of FIG. 2A with mating elements partially engaged.
Figure 2C:
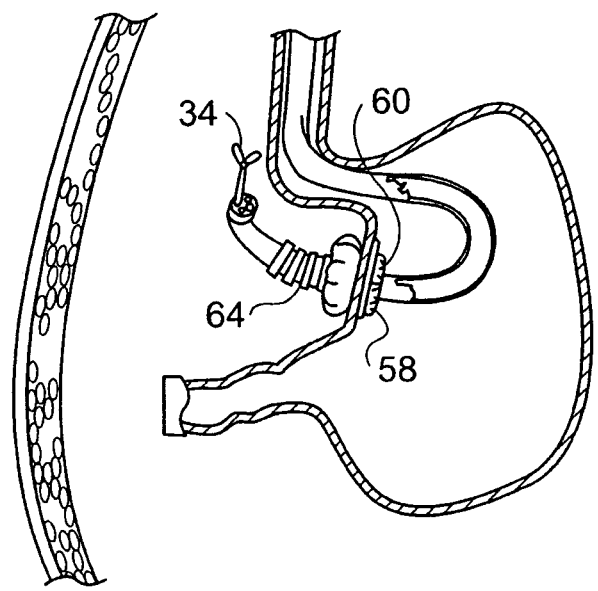
FIG. 2C is a partially transparent view of the transluminal device of FIG. 2A with the mating elements fully engaged.

FIGS. 1 through 2C illustrate an exemplary embodiment of a transluminal device 20 with an integrated port 22 for mating with an anatomic structure. As shown in FIGS. 2A and 2B, the transluminal device can access a body cavity 26 through an opening, for example, in the gastric wall 28. In this case, port 22 includes one or more mating elements 30 that can mate with wall 28 and/or create a seal to inhibit passage of biological materials between the gastrointestinal tract 32 and body cavity 26. With port 22 in place, the distal end of the transluminal device and/or surgical tool 34 can access body cavity 26. While access through the stomach wall is illustrated in FIGS. 2A though 2C, the methods, devices, and systems described herein can be used to traverse a variety of anatomic structures, such as, the wall of the intestine or vagina. In addition, while the discussion of systems and methods below may generally refer to "surgical tools," "surgery," or a "surgical site" for convenience, the described systems and their methods of use are not limited to tissue resection and/or repair procedures. In particular, the described systems can be used for inspection and diagnosis in addition, or as an alternative, to surgery.

Referring now to FIG. 1, device 20 can include a guide tube or elongate body 38 extending between a proximal end 40 and a distal end 42 that includes at least one channel 43 for the passage of surgical instruments, such as, for example, tool 34 (FIG. 2C) and/or optical device (together generally referred to herein as "surgical instruments"). Device 20 can include one, two, three or more than three channels that can house one or more surgical tools. In another aspect, optics or optical device can be integrated into body 38 as described in more detail below.

The distal tip 44 of body 38 can have a blunt, atraumatic shape to minimize tissue damage during insertion. In addition, the distal tip can have a tapered configuration to facilitate insertion of device 20 through an incision or body lumen. In another aspect, the shape of the distal tip can also help to enlarge an opening in the anatomic wall. For example, the distal tip can be used as a dilator. As illustrated in FIGS. 1 through 2C, a user can insert the transluminal device over a guide wire 36 until the distal tip reaches the anatomic wall. A small opening in the wall can first be created via electrosurgical energy and/or mechanical cutting. A clinician can then use the distal tip of the transluminal device to enlarge the opening by pushing the tapered distal tip through the anatomic wall. While the dilator is described as "tapered," in one aspect, the distal tip can have a blunt surface that is used as a dilator. For example, the distal-most surface of the tip can have a flat or planar configuration. In still another aspect, the distal tip can be expanded (e.g., via inflation or mechanical expansion) to provide dilation.

Figure 3:
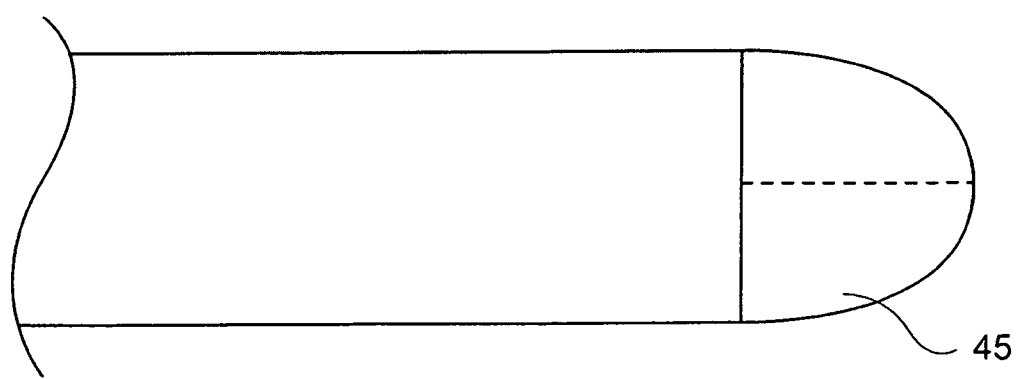
FIG. 3 is a side view of another embodiment of a transluminal device described herein.

In addition, the distal tip 44 can comprise an obturator that caps the end of channel 43 and prevents ingress of biological materials during insertion of device 20. Once the distal tip of the device moves at least partially passed the anatomic wall, the distal end of at least one of the channels in body 38 can be opened. For example, the obturator can be detached, pierced, degraded, and/or broken to permit access into body cavity 26. In one aspect, the obturator can be detached and withdrawn proximally through the transluminal device. Alternatively, FIG. 3 illustrates a breakable or pierceable membrane 45 configured to seal the end of the device during introduction. A surgical tool can be pushed against the obturator to break open or pierce the distal end of the device. While a single slit is illustrated in FIG. 3, the obturator could include multiple slits or break points. In yet another aspect, the obturator can be formed of an at least partly bioadsorbable or dissolvable material. In use, a physician can push the bioadsorbable material out of the end of the guide tube to open the guide tube channels. Alternatively, the bioadsorbable material can be fast dissolving and the guide tube channels can open when biofluids (e.g., blood or stomach acid) dissolve the obturator. In still another embodiment, non-bioadsorbable materials are used and the obturator can remain attached to the distal end of body 38. For example, a clinician can move the obturator away (e.g., pivot, rotate, and/or translate) from the distal opening while the obturator remains mated with the transluminal device. In yet another embodiment, the obturator could be partly degradable or broken into pieces small enough to allow passage through the GI tract.

To assist with creating and opening a passageway through the anatomic wall, the distal tip can be formed, at least in part, of a transparent or translucent material to permit visualization. In one such aspect, an endoscope or other optical device is placed within a channel of the device to permit visualization. Alternatively, optics can be integrated into the transluminal device at a location that permits visualization through the obturator. However, visualization need not be achieved through the obturator. For example, visualization can be achieved from a more proximal location. In one such aspect, a visualization portal 48 allows a user to view the anatomic wall as the distal portion of the device is inserted through the wall. Portal 48 can have an angled configuration to facilitate viewing. While portal 48 is illustrated as fixed relative to body 38, in another aspect, the portal or optics could be extendable and/or movable to allow a user to adjust their point of view. In addition, or alternatively, an optical device can be delivered separately from the transluminal system.

As mentioned above, the transluminal device can include a visualization portal or window 48 positioned proximally from the distal end of the device. In one aspect, the visualization window is proximal of the first and/or second mating features. In use, window 48 allows a user to see the port, mating features, and/or surrounding anatomy. In a further aspect, the transluminal device includes a channel for receiving an optical device, where the channel extends to window 48. In another aspect, the optical channel can include first and second branch, where the first branch extends to window 48 and the second branch extending to a distal window or opening in the transluminal device (not illustrated). In use, a clinician can view a portion of the procedure (e.g., piercing and mating with the anatomic wall) through proximal window 48 and can then change the position of the optical device to a distal window or opening for a different part of the procedure (or to allow a different view of the piercing and mating steps).

While the obturator is generally described as "closed," the obturator and/or an adjacent portion of the device can include, in one aspect, an opening for receiving a guide wire. Additionally, or alternatively, other devices, such as for example, a cutting tool (e.g., needle knife) can be extended through the distal end of the device prior to opening channel 43. In yet another aspect, the distal portion of the device can include an opening for delivering insufflation or deflation fluid. After the obturator has moved through the anatomic wall, delivery of insufflation gas can expand body cavity 26 to enlarge the working space.

As mentioned above, transluminal device 20 can include an integrated port 22 to hold the transluminal device in position relative to the anatomic wall and/or to define a point of reference with respect to the anatomy. Port 22 can additionally form a seal with the anatomic wall to inhibit passage of biological materials. In one aspect, port 22 is defined by at least one mating element 30, and in another aspect, device 20 includes two mating elements 30a, 30b. Body 38 can be advanced through the anatomic wall until the wall is positioned between proximal and distal mating elements 30a, 30b. The mating elements can then be configured to prevent at least the outer surface of the body from moving relative to the wall and/or can form a seal that inhibits passage of biological materials.

In one aspect, increasing the diameter of the mating elements inhibits movement of the mating elements with respect to the anatomic wall. For example, at least one of the mating elements 30a, 30b can be defined by a radially expandable balloon. When inflated, the increased diameter of the balloon inhibits further insertion, or withdrawal, of the transluminal device through the opening in the anatomic wall.

FIG. 1 illustrates a balloon 31 defining distal mating element 30a. Balloon 31 mates with the body 38 of device 20 and can expand in a radial direction when inflated. Generally, balloon 31 can expand from a first size that allows passage through an opening in the anatomic wall to a second, larger size that inhibits withdrawal of the device through the opening in the anatomic wall. While a single balloon is illustrated, multiple balloons could define distal mating element 30a. In addition, balloon 31 need not extend around the full circumference of body 38, a balloon can extend around only a portion of body 38 to inhibit passage of the transluminal device.

One skilled in the art will appreciate that a variety of balloons and balloon materials can be used. In one aspect, the balloon expands by stretching and is formed, at least in part, by material then can increase in surface area. Alternatively, the balloon can be formed, at least in part, of non-stretchable, flexible material. Filling the balloon with fluid increases the volume of the non-stretchable balloon. A variety of medical grade materials, such as, for example, polymers, elastomers, and/or metals can be used to construct the balloons.

In another aspect, the mating element can be defined by a flange, such as, for example, flange 56 of proximal mating element 30b. Flange 56 can have a first configuration for insertion of the transluminal device into a patient and through a lumen, and a second position for mating with the anatomic wall. For example, flange 56 can include multiple segments 58 that lie against the outer surface of body 38 while in the first configuration and which extend radially into the second configuration. As illustrated in FIGS. 2A through 2C, segments 58 are movably mated at their distal ends with body 38 via, for example, a hinge. Alternatively, the flange segments can be defined by a flexible or deformable material and can be bent into the desired configuration. In addition, the flange need not have a planar configuration. For example, the flange could have a "D" cross section or a "T" shape.

Movement of segments from the first configuration to the second configuration can be achieved in a variety of ways. In one embodiment, a balloon can be expanded to move the segments of the flange into the second position. FIG. 2C illustrates balloon 60 inflated to push flange segments 58 into a mating configuration where the outer diameter of the flange is larger than the opening created in the anatomic wall. In another aspect, the flange can be directly articulated, via, for example a control wire. In addition, while flange 56 is described as the proximal mating member, other mating features could be used in addition, or as an alternative, to flange 56 and balloon 60, examples of which are described below with respect to a stand alone or detachable port.

Device 20 can further include surface features that provide tactile feedback. With respect, to FIG. 2C, ridges 64 positioned on the outer surface of the device can provide tactile feedback as the ridges move through the opening created in the anatomic wall. In one aspect, the outer diameter of the ridges is greater than the outer diameter of the distal tip or obturator of the device such that as the ridges reach the opening created in the anatomic wall, increased pressure is required to move the device through the opening. While multiple ridges are illustrated, a single ridge or more than one ridge can be positioned on body 38. In addition, the ridges need not extend around the full circumference of the device as long as a cross-sectional width measured across the surface feature is larger than the opening in the anatomic wall. Moreover, while the surface features are described as ridges, other surface feature shapes, such as, for example, one or more recesses, bumps, and/or threads can provide tactile feedback.

Distal mating feature 30a can also provide tactile feedback to indicate that the anatomic wall is positioned between mating features 30a, 30b. In one aspect, balloon 31, when un-inflated has a cross-sectional width sufficient to create tactile feedback as the un-inflated balloon moves through the opening in the anatomic wall. In yet another embodiment, the proximal mating feature, prior to increasing in width, can define a stop that inhibits further movement of the device through the opening in the anatomic wall. For example, mating feature 30b, when in the insertion configuration can have a cross-sectional width greater than the opening in the anatomic wall and/or greater than the cross-sectional width of the surface features or first mating element. When the proximal mating feature reaches the opening in the anatomic wall, the width of the proximal mating feature can inhibit accidental over insertion of the device. In yet another embodiment, the user can expand the proximal mating feature, for example after encountering the first ridge, such that the expanded proximal mating element acts as a stop. When the expanded proximal mating element reaches the anatomic wall, further insertion is inhibited, indicating to a user that the anatomic wall is situated between the proximal and distal mating elements. The distal mating element can then be expanded to mate with the anatomic wall.

The various mating features described herein can include coatings, covers, and/or surface features to assist with mating. In one aspect, the surface of a mating element can have a sticky, rough, and/or non-planar surface to faciliate pinching or grabbing tissue. In another aspect, a hydrophilic coating or swellable polymer or jell can be positioned on a mating element to facilitate fluid sealing. In a further aspect, an antibiotic material can be positioned on any of the disclosed surfaces of the mating elements, ports, and/or transluminal devices.

With respect to FIG. 1, proximal end 40 of device 20 can have a variety of configurations for receiving and/or controlling surgical tools, delivering inflation fluid, and/or mating with a frame of reference. In one exemplary aspect, the proximal end of the device includes a bite block 66 to hold the device in place with respect to a patient. However, while a bite block is illustrated, the device can additionally or alternatively be mated with an operating table and/or frame. One skilled in the art will appreciate that the proximal portion of device 20 can have a variety of configurations depending on the intended use of the transluminal system. U.S. Non-Provisional patent application Ser. No. 12/078,956, entitled "Medical Rectator and Stabilizing Assembly and Related Methods of Use," includes descriptions of bite blocks and retractors that may be used with embodiments disclosed herein. The complete disclosure of that application is incorporated herein by reference.

In another embodiment, discussed in more detail below, the port is movably mated with the transluminal device. For example, the body of the port can move along a portion of the length of the transluminal device. In use, at least one mating element on the port can mate with an anatomic wall and the transluminal device can then be advanced through the anatomic wall while the port remains fixed with respect to the anatomic wall.

Figure 4B:
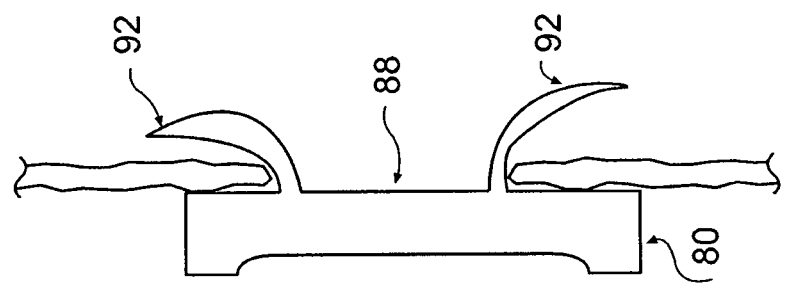
FIG. 4B is a side view of the port of FIG. 4A mated with an anatomic wall.
Figure 4A:
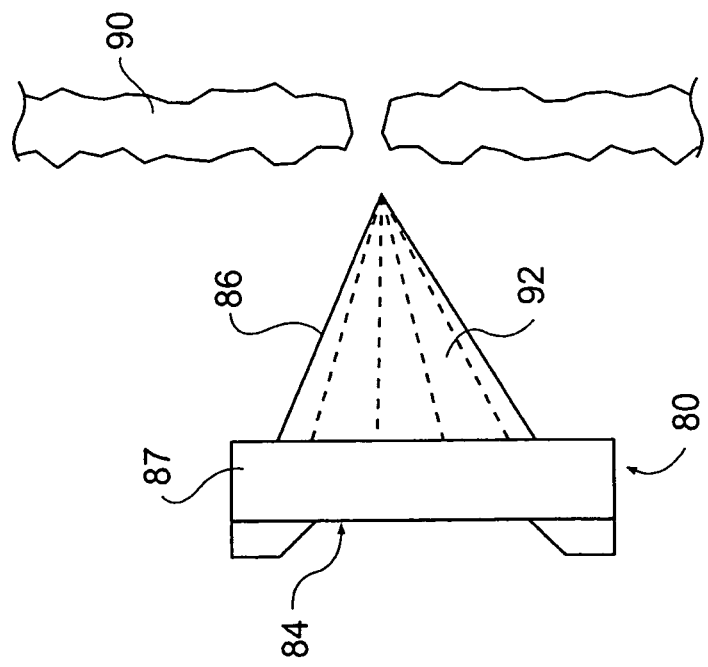
FIG. 4A is a side view of one embodiment of a port described herein.

In yet another embodiment, a stand-alone or detachable port is described. FIGS. 4A and 4B illustrate one exemplary embodiment of a port 80 that can be implanted in an anatomic wall to permit the passage of a transluminal device therethrough. Instead of integrating mating elements into device 20, port 80 can include mating elements, such as, for example, proximal and distal mating elements 30a, 30b described above. Port 80 can mate with the anatomic wall and allow passage of a transluminal device therethrough. In use, port 80 can first be implanted (e.g., with a first device), and then a different device (e.g., a transluminal device) can be inserted through the implanted port. Alternatively, port 80 can be delivered and/or implanted using a transluminal device and then the transluminal device can be inserted through the port.

Port 80 can include a proximal surface 84 having a proximal opening and a distal surface 86 that can be opened to permit passage of the transluminal device. In addition, port 80 can define an aperture or lumen 88 sized and configured to receive a transluminal device. In one aspect, the distal surface of port 80 is configured to facilitate insertion of the port through an anatomic wall. The distal surface can change from an insertion configuration having a generally closed distal end to an opening configuration for allowing passage of the transluminal device. In the closed configuration, distal surface 86 can act in a manner similar to the distal tip of device 20 described above. For example, the port can have a tapered distal surface for insertion through a small opening in an anatomic wall 90. As the tapered surface moves through the opening, the distal surface can act as a dilator to enlarge the opening in wall 90.

Once the distal surface moves through and/or enlarges the opening in the anatomic wall, the distal surface can open and mate with the anatomic wall. In one aspect, anatomic wall 90 is mated between proximal and distal mating surfaces defined by a portion of port body 87 and the distal surface 86, respectively. For example, as shown in FIG. 4B, the distal surface 86, can comprise articulating flange segments 92 such that the distal surface of the port can be moved from a tapered configuration to a splayed configuration in which the distal ends of flange segments 92 pivot or bend outward to mate with tissue. In particular, wall 90 can be held or pinched between flange segments 92 and the body of port 80. When opened, flange segments 92 can have a cross-sectional width that is greater than the tapered portion of the distal surface in the closed configuration and/or greater than the opening created in the anatomic wall.

Movement of flange segments 92 can be achieved in a variety of ways. In one aspect, port 80 can include a balloon that expands and articulates flange segments 92. In another embodiment, the segments can be actuated by a separate device. For example, a user can partially implant port 80 by pushing distal surface 86 through wall 90. A transluminal device can then be pushed against the inner surface of flange segments 92 and used to expand the segments. In another aspect, the transluminal device can include an expandable structure, such as, for example, a balloon to move segments 92 into the mating configuration. However, an expandable structure is not required. For example, a blunt distal end of the transluminal device can expand the flanges as the device is move through lumen 88. The distal end of the transluminal device can then be articulated to push the flange segments into a mating configuration. In one aspect, the expanded shape could be biased in the mating configuration. Through removal of a restrained, the flange could be allowed to expand into the mating configuration.

Figure 5:
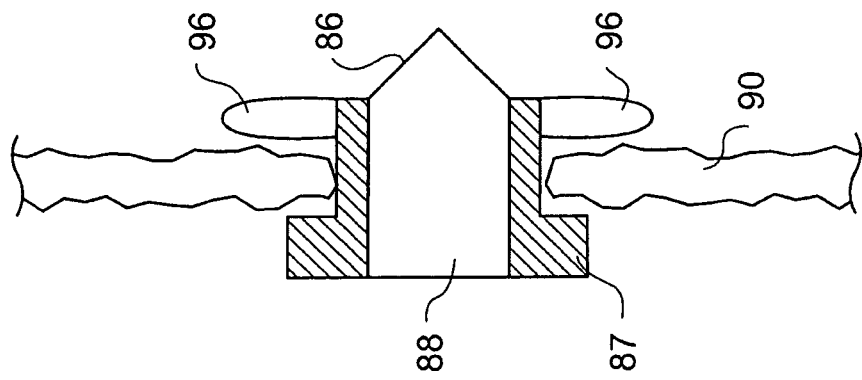
FIG. 5 is a cross-sectional view of another embodiment of a port described herein.

A variety of alternative mating feature are also contemplated. In one aspect, instead of flange segments, port 80 can include a balloon or balloons 96, that when expanded, mate port 80 and wall 90. FIG. 5 illustrates balloon 96 having a donut-like configuration. Expanding balloon 96 can inhibit withdrawal of port 80 while the cross-sectional width of body 87 of port 80 can inhibit further insertion of the port. In particular, anatomic wall 90 can be mated between the body of the port and balloon 96.

The port of FIG. 5 can be inserted in a manner similar to that described above. However, instead of distal surface 86 defining a mating element, the distal surface can define an obturator that is removed, detached, degraded, opened, moved, and/or broken after the port passes through wall 90. For example, distal surface 86 can include the features of the obturator described with respect to device 20. In one aspect, balloon 96 is positioned on port 80 such that the balloon can be expanded and the port mated with wall 90 without opening distal surface 86. The obturator-distal surface 86 can then be opened to allow passage of the intraluminal device.

Figure 6B:
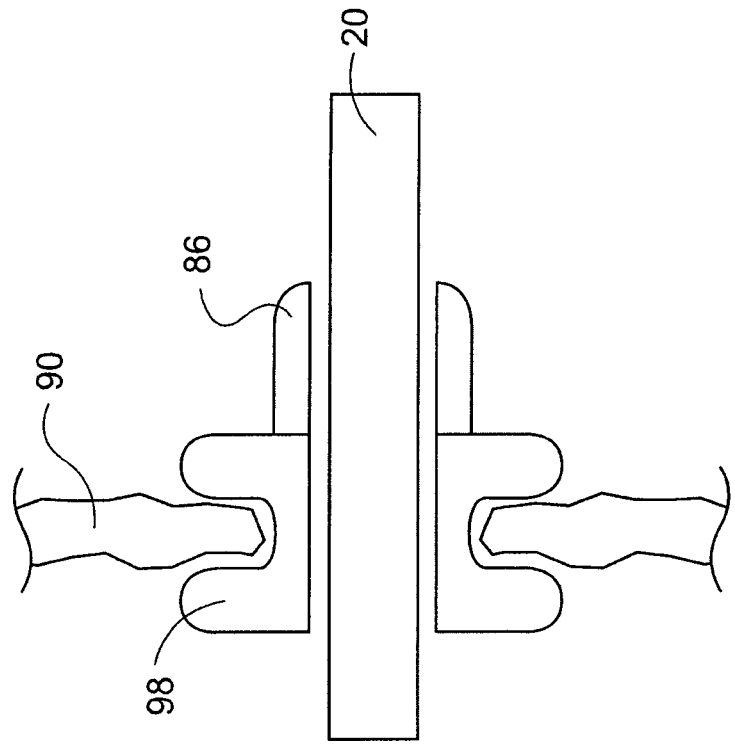
FIG. 6B is a cross-sectional view of the port of FIG. 6A mated with an anatomic wall.
Figure 6A:
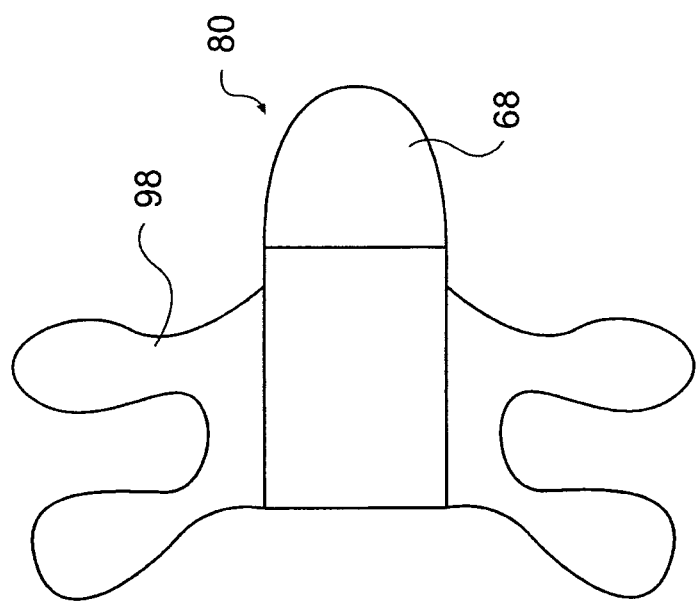
FIG. 6A is a side view of yet another embodiment of a port described herein.

In another embodiment of port 80, a balloon or balloons can define the proximal and/or distal mating elements. FIGS. 6A and 6B illustrate port 80 including a double-lobed balloon 98. The port can be inserted as described above and then balloon 98 can be expanded to mate the port with wall 90. While a single balloon is illustrated as defining the proximal and distal mating elements, multiple balloons could be used. For example, a proximal and a distal balloon can be inflated on either side of wall 90 to mate port 80 with wall 90.

Figure 7B:
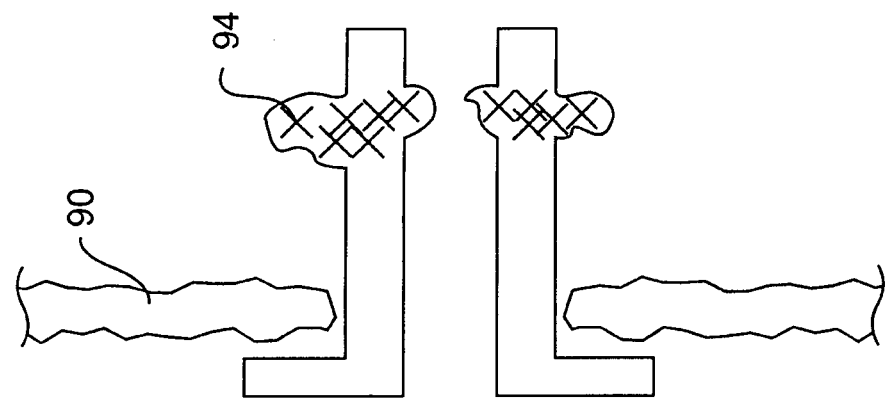
FIG. 7B is a cross-sectional view of the port of FIG. 7A mated with an anatomic wall.
Figure 7A:
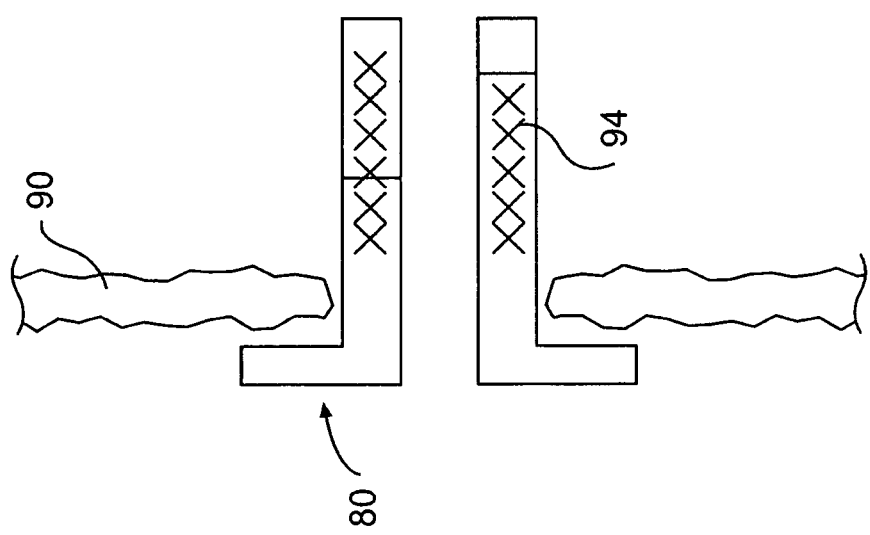
FIG. 7A is a cross-sectional view of another embodiment of a port described herein.

The proximal and distal mating elements can be defined by a variety of other radially expandable structures in addition, or as an alternative, to balloons. Other exemplary radially expandable structures include malecots and/or wire mesh structures that radially expand when longitudinally compressed. FIGS. 7A and 7B illustrate a distal mating element formed from mesh 94. When longitudinally compressed, the mesh portion of the port expands radially. The mesh mating member can be controlled in a variety of ways, including, for example, via a pull wire.

In another aspect, the proximal and/or distal mating elements do not radially expand. The outer surface of the port can include threads that mate the port with the anatomic wall. The port can be rotated as it is inserted to assist with pushing the anatomic wall over the threads. However, the port need not be rotated. FIG. 8A illustrates threads 95 defining a mating element for mating port 80 with anatomic wall 90. Note that separate proximal and distal mating elements are not required. In another aspect, the outer surface of the port can include a recess having a diameter smaller than the opening in the anatomic wall, while the distal mating surface has a width greater than the opening in the wall. Where the anatomic wall is at least somewhat resilient, the distal mating surface can be pushed through the opening created in the wall to allow the wall to seat in the recess in the outer surface of the port. FIG. 8B, illustrates a rigid distal mating element 30b and a recess 33 with wall 90 mated within recess 33 of port 80.

Figure 9B:
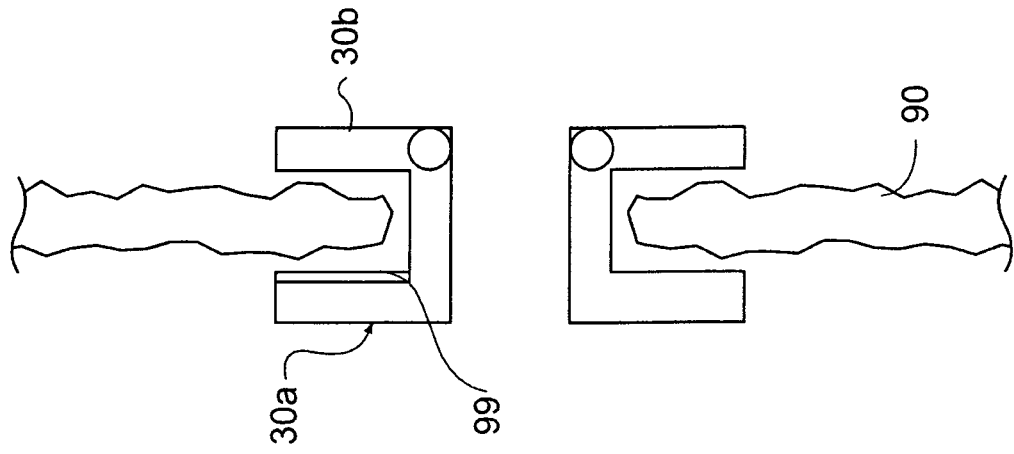
FIG. 9B is a cross-sectional view of the port of FIG. 9A mated with an anatomic wall.
Figure 9A:
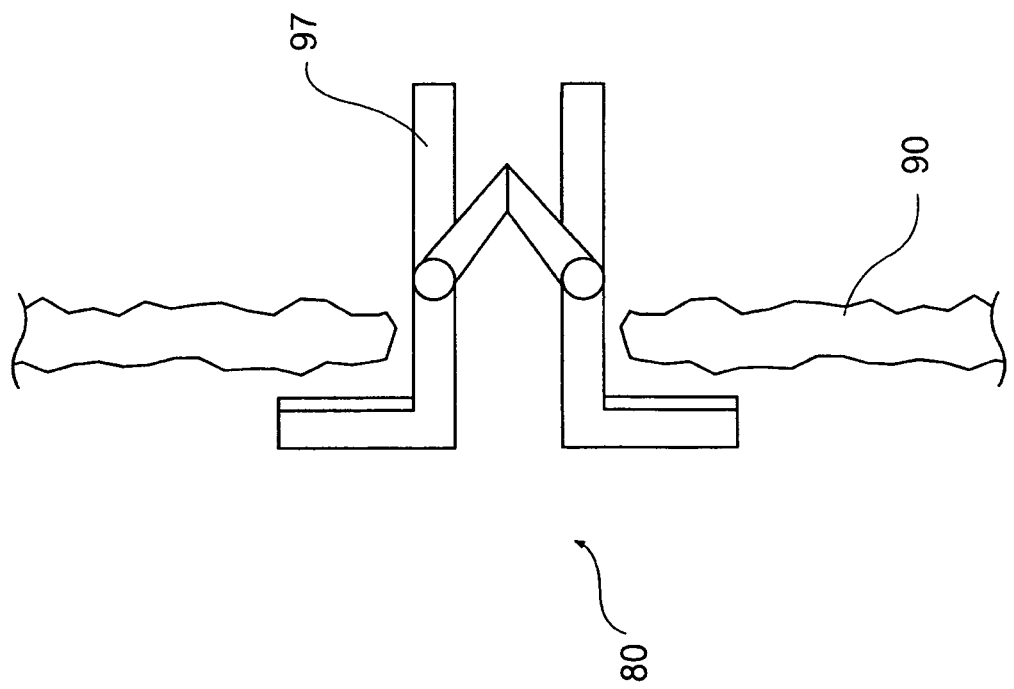
FIG. 9A is a cross-sectional view of still another embodiment of a port described herein.

In another aspect, the proximal and/or distal mating elements can incorporate a magnet to hold the mating elements in the mated configuration and/or to move the mating elements into the mating configuration. For example, a proximal mating element can include a magnet that attracts the distal mating element of the port. FIGS. 9A and 9B illustrate a distal mating element 30b defined at least in part by a ferrous material 97. Once the distal mating element moves into the mating configuration, a magnet 99 of the proximal mating element can attract ferrous material 97 and mate port 80 with tissue wall 90. The strength and type of magnet can be chosen depending on anatomic wall thickness and/or the intended use of the system. In one aspect, both proximal and distal mating elements include magnets.

As mentioned above, port 80 can be sized and configured to receive a transluminal device. The lumen defined by port 80 (e.g., lumen 88 illustrated in FIGS. 4B and 5) can, in one aspect, have a varying diameter such that differently sized devices or varying diameter devices can pass through lumen 88 while inhibiting the passage of biological materials. In one aspect, a balloon (not illustrated) positioned within lumen 88 can be expanded/contracted to adjust the diameter of the passageway through port 80. Alternatively, a flexible seal (not illustrated), such as, for example, a wiper seal can extend around the inner surface of lumen 88. As the transluminal device is passed through lumen 88, the flexible seal can bend, deform, and/or flex to expand the inner diameter of the lumen. In still another aspect, a flexible membrane (not illustrated) can be positioned within lumen 88. As the transluminal device is moved through port 80, the device can puncture the membrane, which then forms a seal around the outer surface of the transluminal device.

As described above, port 80 can be implanted prior to insertion of the transluminal device. In another aspect, port 80 can be detachably or movably mated with the transluminal device. Regardless, the port and the transluminal device can be configured to move relative to one another to permit advancement of the distal end of the transluminal device to a target location.

FIG. 10A illustrates port 80 positioned on the end of transluminal device 100. After mating port 80 with wall 90 as described above, port 80 remains fixed relative to wall 90 and transluminal device 100 can be advanced further into the body cavity. As shown in FIG. 10B, the transluminal device can be inserted and/or withdrawn relative to port 80 to position the distal end of the transluminal device 100 at a desired location within body cavity 26.

Figure 11:
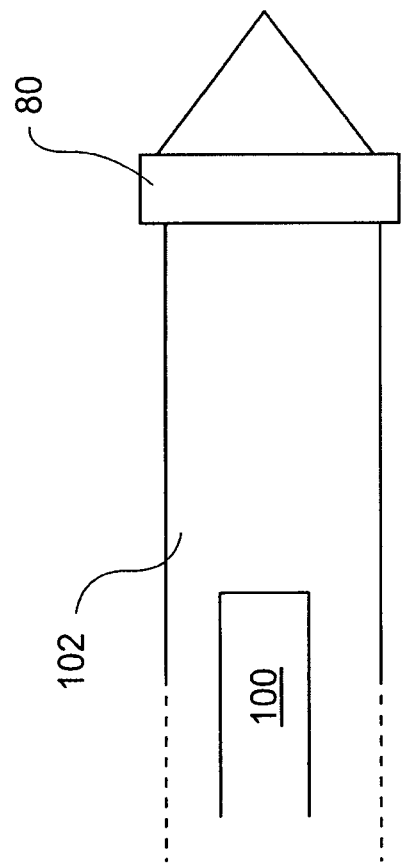
FIG. 11 is a partially transparent view of another embodiment of a port described herein.

In another aspect, port 80 can further comprise a tubular body that defines a passageway between a surgical opening or natural body orifice and the lumen of port 80. FIG. 11 illustrates a guide tube or sheath 102, the distal end of which mates with port 80. The port, including sheath 102, can be inserted into a patient and mated with an anatomic wall. In one aspect, sheath 102 is articulating and the a user can maneuver the sheath/port system to the anatomic wall and then implant port 80. For example, sheath 102 can include an articulating section that is controlled by a user. After implanting port 80, transluminal tool 100 can then be directed through sheath 102 and port 80 to a body cavity. Alternatively, a surgical tool, such as a transluminal device can be used to guide and/or implant the sheath/port system.

Sheath 102 can provide a barrier to ingress of biological materials between the entrance to a patient's body and the anatomic wall. One skilled in the art will appreciate that a variety of flexible materials can be used to construct sheath 102. In addition, sheath 102 can be expandable. During insertion, the sheath can be a first diameter that is expanded to a second, larger diameter when transluminal device 100 is inserted through the sheath.

Figure 12:
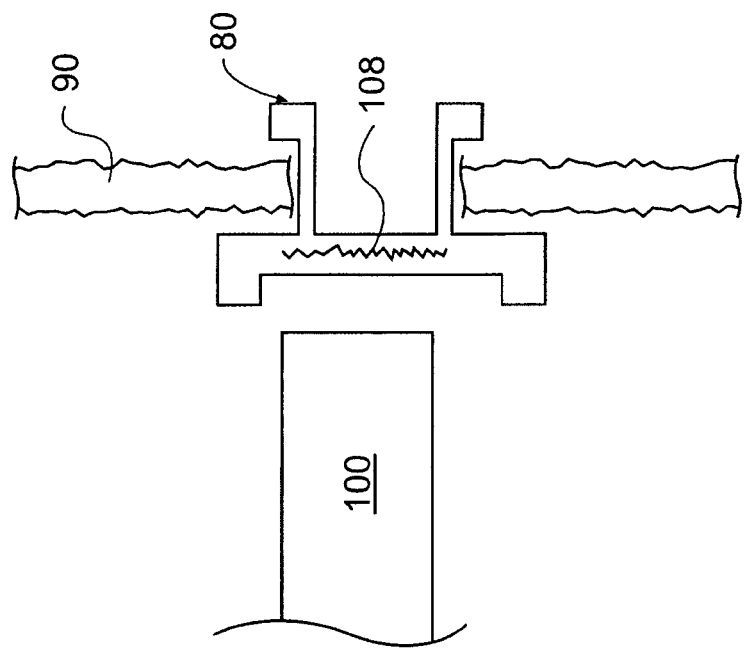
FIG. 12 is a cross-sectional view of yet another embodiment of a port described herein.

In still another embodiment, port 80 is implanted with a first device and a second device (e.g., a transluminal device) is then inserted through the port to perform a procedure within a body cavity. Port 80 can include a seal or valve to inhibit passage of biological material through the port lumen prior to insertion of the transluminal device. FIG. 12 illustrates port 80 mated with wall 90 and including a check valve 108 to prevent the passage of biological material. When the transluminal device approaches the port, the transluminal device opens the check valve and passes through the port. To minimize the amount of biological material that accompanies the transluminal device through the port, the transluminal device can clean and/or disinfect the check valve prior to passage through the port. For example, the distal end the transluminal device can include an opening for delivery of saline solution and/or antibiotic. One skilled in the art will appreciate that a variety of alternative sealing mechanisms can be substituted for the check valve, including a membrane or balloon.

Regardless of the configuration of port 80, the port can, in one embodiment, movably mate with the transluminal device. For example, the transluminal device and port can mate via a mechanical and/or frictional fit that can act as a seal between the outer surface of the transluminal device and the inner surface of the port. However, the mating between the outer surface of the transluminal device and the inner surface of the port can allow rotational and/or longitudinal movement of the transluminal device with respect to the port. In another aspect, the port can include a tether or guide wire to facilitate directing the transluminal device to the port.

In another embodiment, the port is movably mated with the transluminal device. For example, the body of the port can move along a portion of the length of the transiuminal device. In use, at least one mating element on the port can mate with an anatomic wall and the transluminal device can then be advanced through the anatomic wall while the port remains fixed with respect to the anatomic wall.

In one aspect, the port can slide between a first proximal and a second distal position along the length of the transluminal device. For example, the port can include a sheath on which the first and/or second mating elements reside. The sheath can slide over an outer surface of the transluminal device to permit movement of the transluminal device with respect to the port. The transluminal device and/or port can include stops that constrain movement of the port between the first and second position.

The movably mated port can include the various features of the integral port described above or the detachable port described above. In one aspect, the connection between the transluminal device and the port allows relative longitudinal movement between the transluminal device and the port. In another aspect, the movable connection inhibits relative movement in other directions. For example, the port can be prevented from moving transversely and/or rotating with respect to the transluminal device.

Where the movably mated port includes a balloon, the transluminal device can include an inflation channel extending to an opening in the port. In use, the balloon can be expanded via the inflation channel and then the port allowed to move relative to the transluminal device after expansion. For example, the inflation channel can extend to an opening in the outer surface of the transluminal device which is aligned with an opening in the port for receiving inflation fluid. When the port moves relative to the transluminal device, the opening in the port can be blocked by the outer surface of the transluminal device, thereby inhibiting deflation of the balloon. Similarly, where the mating elements are mechanically expanded, a lever or other mechanism on the transluminal device can expand the mating element(s) on the port.

In one embodiment, a lock can inhibit movement between the movably mated port and transluminal device. In one aspect, a mechanical interlock (e.g., a protrusion and recess, latch, threaded connection) can inhibit relative movement between the transluminal device and port. In another aspect, a frictional or interference fit can form a temporary lock between the transluminal device and port. In still another embodiment the port and transluminal device can be adhered or tied to one another. In particular, they can be sutured to one another.

In use, the port can be locked to the transluminal device during insertion of the system and during mating of the port with an anatomic wall. A user can then disengage the lock and allow the port to move relative to the transluminal device. In one aspect, the lock can be controlled from a proximal end of the transiuminal device, for example, via a pull wire. Alternatively, a tool can be inserted through the transluminal device to detach the port. For example, where the port and transluminal device are sutured to one another the tool can break or cut the suture.

In yet another embodiment of port 80, the port can form a suction seal with the anatomic wall prior to creating an opening. FIG. 13 illustrates an opening 110 on the distal surface 86 of port 80 for providing suction. Opening 110 can extend around the area where an opening is to be created in the wall. For example, a continuous opening can extend around the distal surface adjacent to the outer perimeter of the distal surface. However, more than one suction opening can be used and/or a non-continuous opening can mate port 80 and wall 90. Applying suction through opening 110 can create a seal between the port and tissue that prevents ingress of biological materials and reduces the amount of biological materials that pass through an opening created in the anatomic wall. In addition, or alternatively, suction can hold the port in place before, during, or after the creation of an opening in the anatomic wall.

In another aspect, opening 110 can be defined by an inner and outer body. As illustrated in FIG. 14, an inner tubular body 112 is positioned within a channel defined by an outer tubular body 114. A vacuum can be established between the inner and outer bodies 112, 114 to apply suction to wall 90 and mate therewith. In one aspect, the outer body can be defined by port 80 and inner body 114 can be defined by a transluminal device. Alternatively, both the inner and outer bodies can be defined by the port or by the transluminal device.

In use, opening 110 between the inner and outer bodies 112, 114 can contact the tissue wall and form a suction seal therewith. An aperture can then be created in the wall, and the inner body can be advanced through the wall. The vacuum can then establish a seal with anatomic wall 90 during insertion of the transluminal device through the opening in the tissue wall. In other words, instead of the mating element or elements described above, the vacuum between the inner and outer tubular bodies can mate the transluminal system with the anatomic wall.

Suction can additionally or alternatively be provided on a more proximal or side surface of the port and/or on the transluminal device. In one aspect, suction can be used to stabilize the port or transluminal device by mating the port or transluminal device with an anatomic structure. As shown in FIGS. 15A and 15B, transluminal device 100 can include at least one opening 110 on an outer sidewall surface for mating with an anatomic wall and holding the transluminal device in place relative to the wall. With the transluminal device stabilized, a passage can then be created in the wall.

For application or creation of suction or a vacuum a pump can be used with the systems described herein. The pump can include any of the know devices for reducing pressure and creating suction including mechanical pumps, hospital or operating room suction ports, syringes, and/or other such devices.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

The invention claimed is:

1. A transluminal system comprising:
an elongate guide tube extending between a proximal portion and a distal portion and including at least one channel for the passage of a tool, the guide tube including an articulation section driven by a proximal control mechanism; and
a port movably mated with the guide tube and including at least one mating element for mating with an anatomic wall to maintain an opening in the anatomic wall, wherein the port permits movement of the guide tube with respect to the port after mating the port with the anatomic wall;
wherein the elongate guide tube includes a surface feature having a diameter greater than the opening, the surface feature being moveable through the opening with the elongate guide tube such that the surface feature directly contacts the anatomic wall; and
wherein the elongate guide tube includes a side portal proximal to the port, the side portal having an angled configuration to permit viewing the port as it mates with the anatomic wall.

2. The system of claim 1, wherein the port includes a distal surface.

3. The system of claim 2, wherein the distal surface defines part of an obturator.

4. The system of claim 3, wherein the distal surface is openable to permit passage of the guide tube through the port.

5. The system of claim 3, wherein the at least one mating element is mateable with tissue without opening the port.

6. The system of claim 1, wherein the at least one mating element is radially expandable.

7. The system of claim 6, wherein the at least one mating element includes a flange driven by expansion of a balloon.

8. The system of claim 7, wherein the balloon is positioned between the flange and a body of the guide tube.

9. The system of claim 8, wherein the flange includes multiple segments that lie against the balloon along an outer surface of the elongate guide tube.

10. The system of claim 1, wherein the side portal includes a first window positioned proximally of the port for viewing at least one of the port and the adjacent environment.

11. The system of claim 10, wherein the guide tube includes a channel extending to the first window for passage of an optical device.

12. The system of claim 11, wherein the channel includes a first branch for viewing via the first window and a second branch that extends to at least one of a second distal window and a distal opening.

13. The system of claim 1, wherein the surface feature is sized and shaped to provide tactile feedback corresponding to the contact with the anatomic wall for determining a location of the at least one mating element relative to the opening of the anatomic wall during insertion of the elongate guide tube through the opening in the anatomic wall.

14. The system of claim 1, wherein the at least one mating element includes a magnet.

15. The system of claim 14, wherein a first and a second mating element are positioned to receive an anatomic wall therebetween.

16. The system of claim 1, wherein a first and a second mating element are adapted to magnetically mate with one another.

17. The system of claim 1, wherein the port is constrained between a first proximal position and a second distal position along a length of the guide tube.

18. The system of claim 17, wherein the port can slide along a length of the guide tube between the first and second positions.

19. The system of claim 18, further comprising a locking mechanism for inhibiting relative movement between the guide tube and port.

20. The system of claim 1, wherein the guide tube includes multiple passageways for the passage of at least two tools.

21. The system of claim 1, wherein the surface feature includes a plurality of ridges, and at least one of the plurality of ridges has a diameter greater than the at least one mating element in a collapsed configuration.

22. The system of claim 21, wherein at least one of the plurality of ridges includes an annular ridge.

23. A transluminal system comprising:
an elongate guide tube extending between a proximal portion and a distal portion and including at least one channel for the passage of a tool, the distal portion of the guide tube having at least one distal opening;
a port including a proximal mating element and a distal mating element for mating with an anatomic wall to maintain an opening in the anatomic wall, the port further including a lumen for receiving at least a portion of the elongate guide tube, and an elongate body extending proximally from the port and defining a passageway for receiving the guide tube, wherein the guide tube is insertable through the passageway and through the port, and wherein the guide tube includes a surface feature having a diameter greater than the opening in the anatomic wall, the surface feature being moveable through the opening in the anatomic wall with the elongate guide tube such that the surface feature directly contacts the anatomic wall;
wherein the proximal mating element includes a pivoting flange configured to pivot away from the lumen and toward the distal mating element at substantially the same time; and wherein the elongate guide tube includes a side portal proximal to the port, the side portal having an angled configuration to permit viewing the port as it mates with the anatomic wall.

24. The system of claim 23, wherein the elongate body is flexible.

25. The system of claim 23, wherein the elongate body includes an articulation section.

26. The system of claim 23, wherein the flange includes multiple segments that lie against an outer surface of the elongate guide tube.

27. A method of traversing an anatomic wall, comprising:
creating an opening in an anatomic wall;
passing at least a portion of an elongate guide tube through the opening, the elongate guide tube movably mated with a port having a proximal-most end and a distal-most end, wherein the proximal-most end of the port includes a first mating element comprising a flange and the distal-most end of the port includes a second mating element, wherein the elongate guide tube includes a side portal proximal to the port, the side portal having an angled configuration to permit viewing the port as it mates with the anatomic wall, and wherein the portion of the elongate guide tube that passes through the opening includes a distal tip and a surface feature having a diameter greater than the opening to contact the anatomic wall;
contacting the anatomic wall with the surface feature;
after contacting the anatomic wall with the surface feature, passing the distal-most end of the port through the opening such that the second mating element is distal to the anatomic wall and the flange is proximal to the anatomic wall;
rotating the flange outward from the port; and
mating the port with the anatomic wall via the rotated flange.

28. The method of claim 27, further comprising the step of opening an obturator located at the distal tip to expose a distal opening of at least one channel of the elongate guide tube.

29. The method of claim 27, wherein the second mating element comprises a balloon, the method further including mating the port with the anatomic wall by radially expanding the balloon.

30. The method of claim 27, further including adjusting the position of the elongate guide tube in the anatomic wall based on tactile feedback.

31. The method of claim 30, wherein at least one of the surface feature and the second mating element provides tactile feedback upon contacting the anatomic wall when passed through the opening in the anatomic wall.

32. The method of claim 27, wherein the flange is rotated prior to contacting the anatomic wall to mate the port with the anatomic wall.

33. The method of claim 27, wherein the flange includes multiple segments that lie against an outer surface of the elongate guide tube.

34. A transluminal system comprising:
an elongate guide tube extending between a proximal portion and a distal portion and having at least one channel, wherein the guide tube includes a distally-located articulation section driven by a proximally-located control mechanism; and
a port having a lumen configured to slidingly receive the guide tube and a first mating element configured to mate a proximal-most end of the port to an anatomic wall to maintain an opening in the anatomic wall, wherein the first mating element includes a flange moveable radially to couple to the anatomic wall;
wherein the elongate guide tube includes a surface feature distal to the first mating element and having a diameter greater than the opening, the surface feature being movable through the opening with the elongate guide tube such that the surface feature contacts the anatomic wall to determine a location of the first mating element relative to the opening; and
wherein the elongate guide tube includes a side portal proximal to the port, the side portal having an angled configuration to permit viewing the port as it mates with the anatomic wall.

35. The system of claim 34, wherein the flange includes a rigid member having an end that moves radially and axially from a location adjacent to the guide tube to a location outward from the guide tube.

36. The system of claim 34, wherein the flange includes a plurality of flange segments that lie against an outer surface of the elongate guide tube, each flange element having a proximal end that is moveable relative to the guide tube.

37. The system of claim 34, wherein the port includes a second mating element located distally relative to the first mating element.

38. The system of claim 37, wherein the second mating element includes a radially expandable balloon.

* * * * *